(12) United States Patent
Deal et al.

(10) Patent No.: US 6,711,440 B2
(45) Date of Patent: Mar. 23, 2004

(54) MRI-COMPATIBLE MEDICAL DEVICE WITH PASSIVE GENERATION OF OPTICAL SENSING SIGNALS

(75) Inventors: Jeffrey T. Deal, Clarence, NY (US); Wilson Greatbatch, Akon, NY (US)

(73) Assignee: Biophan Technologies, Inc., West Henrietta, NY (US)

( * ) Notice: Subject to any disclaimer, the term of this patent is extended or adjusted under 35 U.S.C. 154(b) by 39 days.

(21) Appl. No.: 10/120,922

(22) Filed: Apr. 11, 2002

(65) Prior Publication Data

US 2003/0195570 A1 Oct. 16, 2003

(51) Int. Cl.⁷ .............................................. A61N 1/362
(52) U.S. Cl. ........................................................ 607/9
(58) Field of Search ..................................... 607/1–156

(56) References Cited

U.S. PATENT DOCUMENTS

| | | |
|---|---|---|
| 3,057,356 A | 10/1962 | Greatbatch .................. 128/422 |
| 3,478,746 A | 11/1969 | Greatbatch .................. 128/421 |
| 3,508,167 A | 4/1970 | Russell, Jr. .................. 331/111 |
| 3,669,095 A | 6/1972 | Kobayashi et al. |
| 3,686,958 A | 8/1972 | Porter et al. .................. 73/406 |
| 3,718,142 A | 2/1973 | Mulier |
| 3,789,667 A | 2/1974 | Porter et al. .................. 73/406 |
| 3,825,015 A | 7/1974 | Berkovits |
| 4,012,641 A | 3/1977 | Brickerd, Jr. et al. |
| 4,041,954 A | 8/1977 | Ohara ........................ 128/419 |
| 4,050,004 A | 9/1977 | Greatbatch .................. 363/59 |
| 4,071,032 A | 1/1978 | Schulman |
| 4,091,818 A | 5/1978 | Brownlee et al. ........... 128/419 |
| 4,200,110 A | 4/1980 | Peterson et al. ............ 128/634 |
| 4,210,029 A | 7/1980 | Porter ........................ 73/705 |
| 4,254,776 A | 3/1981 | Tanie et al. .................. 128/421 |
| 4,325,382 A | 4/1982 | Miodownik |
| 4,333,053 A | 6/1982 | Harrison et al. |
| 4,341,221 A | 7/1982 | Testerman |
| 4,379,262 A | 4/1983 | Young |
| 4,432,363 A | 2/1984 | Kakegawa .................. 128/419 |
| 4,450,408 A | 5/1984 | Tiemann |
| 4,476,870 A | 10/1984 | Peterson et al. ............ 128/634 |
| 4,491,768 A | 1/1985 | Slicker |
| 4,545,381 A | 10/1985 | Bournay, Jr. et al. |
| 4,611,127 A | 9/1986 | Ibrahim et al. |
| 4,677,471 A | 6/1987 | Takamura et al. |
| 4,686,964 A | 8/1987 | Yunoki et al. |
| 4,691,164 A | 9/1987 | Haragashira |

(List continued on next page.)

FOREIGN PATENT DOCUMENTS

WO    WO 01/74241    10/2001

OTHER PUBLICATIONS

M. Kusumoto et al., "Cardiac Pacing for the Clincian," Lippincott Williams & Wilkins: (2001); Chapter 1, pp. 9, 12, 18, 22, 24.

(List continued on next page.)

*Primary Examiner*—Scott M. Getzow
(74) *Attorney, Agent, or Firm*—Basch & Nickerson LLP; Michael J. Nickerson

(57) ABSTRACT

An optical sense signal generator for medical device's having a photonic catheter containing optical conductors conducting light energy in two directions between electronics at a catheter proximal end and electrical stimulation and sensing components at a catheter distal end. An optical unit receives light delivered from the catheter proximal end and transmits a first portion of the light while diverting a second portion of the light. The transmitted light is fed to an opto-electrical converter for conversion into electrical stimulation signals. The diverted light is directed to one or more optical modulators that modulate the diverted light output under an applied electrical signal. An electrical circuit generates electrical sense signals corresponding to one or more sensed physiological conditions and provides the signals to the optical modulator(s). This results in modulation of the diverted light output into optical sense signals that are transmitted to the catheter proximal end.

36 Claims, 6 Drawing Sheets

U.S. PATENT DOCUMENTS

| | | | |
|---|---|---|---|
| 4,719,159 A | 1/1988 | Clark et al. | |
| 4,727,874 A | 3/1988 | Bowers et al. | |
| 4,763,075 A | 8/1988 | Weigert | 324/318 |
| 4,784,461 A | 11/1988 | Abe et al. | |
| 4,798,443 A | 1/1989 | Knipe et al. | |
| 4,800,883 A | 1/1989 | Winstrom | |
| 4,804,244 A | 2/1989 | Hasegawa et al. | |
| 4,827,906 A | 5/1989 | Robicsek et al. | 600/17 |
| 4,827,934 A | 5/1989 | Ekwall | |
| 4,858,610 A | 8/1989 | Callaghan et al. | |
| 4,879,992 A | 11/1989 | Nishigaki et al. | |
| 4,880,004 A | 11/1989 | Baker, Jr. et al. | |
| 4,903,701 A | 2/1990 | Moore et al. | |
| 4,911,525 A | 3/1990 | Hicks et al. | |
| 4,930,521 A | 6/1990 | Metzger et al. | |
| 4,934,785 A | 6/1990 | Mathis et al. | |
| 4,987,897 A | 1/1991 | Funke | |
| 4,991,590 A | 2/1991 | Shi | |
| 5,010,888 A | 4/1991 | Jadvar et al. | |
| 5,055,810 A | 10/1991 | deLaChapelle et al. | |
| 5,058,586 A | 10/1991 | Heinze | 128/634 |
| 5,061,680 A | 10/1991 | Paulson et al. | |
| 5,089,697 A | 2/1992 | Prohaska | 250/227.21 |
| 5,113,859 A | 5/1992 | Funke | |
| 5,131,409 A | 7/1992 | Lobarev et al. | |
| 5,154,387 A | 10/1992 | Trailer | |
| 5,158,932 A | 10/1992 | Hinshaw et al. | |
| 5,168,871 A | 12/1992 | Grevious | |
| 5,178,149 A | 1/1993 | Imburgia et al. | |
| 5,214,730 A | 5/1993 | Nagasawa et al. | |
| 5,217,009 A | 6/1993 | Kronberg | |
| 5,217,010 A | 6/1993 | Tsitlik et al. | 128/419 |
| 5,226,210 A | 7/1993 | Koskenmaki et al. | |
| 5,240,004 A | 8/1993 | Walinsky et al. | |
| 5,243,979 A | 9/1993 | Stein et al. | |
| 5,265,602 A | 11/1993 | Anderson et al. | |
| 5,267,564 A | 12/1993 | Barcel et al. | |
| 5,324,310 A | 6/1994 | Greeninger et al. | |
| 5,330,512 A | 7/1994 | Hauck et al. | |
| 5,348,010 A | 9/1994 | Schnall et al. | |
| 5,354,220 A | 10/1994 | Ganguly et al. | |
| 5,370,668 A | 12/1994 | Shelton | |
| 5,387,229 A | 2/1995 | Poore | |
| 5,387,232 A | 2/1995 | Trailer | |
| 5,402,070 A | 3/1995 | Shelton et al. | |
| 5,410,413 A | 4/1995 | Sela | |
| 5,415,653 A | 5/1995 | Wardle et al. | |
| 5,425,373 A | 6/1995 | Causey, III | |
| 5,435,308 A | 7/1995 | Gallup et al. | |
| 5,435,316 A | 7/1995 | Kruse | |
| 5,438,987 A | 8/1995 | Thacker et al. | |
| 5,445,151 A | 8/1995 | Darrow et al. | |
| 5,453,838 A | 9/1995 | Danielian et al. | |
| 5,454,837 A | 10/1995 | Lindegren et al. | 607/9 |
| 5,456,698 A | 10/1995 | Byland et al. | |
| 5,464,014 A | 11/1995 | Sugahara | |
| 5,476,095 A | 12/1995 | Schnall et al. | |
| 5,520,190 A | 5/1996 | Benedict et al. | 128/700 |
| 5,523,534 A | 6/1996 | Meister et al. | |
| 5,569,158 A | 10/1996 | Suzuki et al. | |
| 5,570,671 A | 11/1996 | Hickey | |
| 5,574,811 A | 11/1996 | Bricheno et al. | |
| 5,575,772 A | 11/1996 | Lennox | |
| 5,582,170 A | 12/1996 | Soller | |
| 5,590,227 A | 12/1996 | Osaka et al. | |
| 5,601,611 A | 2/1997 | Fayram et al. | 607/6 |
| 5,603,697 A | 2/1997 | Grundy et al. | |
| 5,604,433 A | 2/1997 | Theus et al. | |
| 5,611,016 A | 3/1997 | Fangmann et al. | |
| 5,619,605 A | 4/1997 | Ueda et al. | |
| 5,626,618 A | 5/1997 | Ward et al. | |
| 5,626,619 A | 5/1997 | Jacobson et al. | 607/5 |
| 5,631,988 A | 5/1997 | Swirhun et al. | |
| 5,634,720 A | 6/1997 | Gallup et al. | |
| 5,649,965 A | 7/1997 | Pons et al. | |
| 5,653,735 A | 8/1997 | Chen et al. | |
| 5,654,317 A | 8/1997 | Fujioka et al. | |
| 5,658,966 A | 8/1997 | Tsukamoto et al. | |
| 5,679,026 A | 10/1997 | Fain et al. | |
| 5,683,435 A | 11/1997 | Truex et al. | |
| 5,697,958 A | 12/1997 | Paul et al. | |
| 5,699,801 A | 12/1997 | Atalar et al. | |
| 5,709,225 A | 1/1998 | Budgifvars et al. | |
| 5,716,386 A | 2/1998 | Ward et al. | |
| 5,723,856 A | 3/1998 | Yao et al. | |
| 5,733,247 A | 3/1998 | Fallon | |
| 5,738,105 A | 4/1998 | Kroll | |
| 5,749,910 A | 5/1998 | Brumwell et al. | |
| 5,752,977 A | 5/1998 | Grevious et al. | |
| 5,755,739 A | 5/1998 | Sun et al. | |
| 5,755,742 A | 5/1998 | Schuelke et al. | |
| 5,759,197 A | 6/1998 | Sawchuk et al. | |
| 5,761,354 A | 6/1998 | Kuwano et al. | |
| 5,766,227 A | 6/1998 | Nappholz et al. | |
| 5,772,604 A | 6/1998 | Langberg et al. | |
| 5,774,501 A | 6/1998 | Halpern et al. | |
| 5,776,167 A | 7/1998 | Levine et al. | |
| 5,776,168 A | 7/1998 | Gunderson | |
| 5,782,241 A | 7/1998 | Felblinger et al. | |
| 5,782,880 A | 7/1998 | Lahtinen et al. | |
| 5,808,730 A | 9/1998 | Danielian et al. | |
| 5,814,087 A | 9/1998 | Renirie | |
| 5,814,089 A | 9/1998 | Stokes et al. | |
| 5,814,090 A | 9/1998 | Latterell et al. | |
| 5,814,091 A | 9/1998 | Dahlberg et al. | |
| 5,817,130 A | 10/1998 | Cox et al. | |
| 5,817,133 A | 10/1998 | Houben | |
| 5,817,136 A | 10/1998 | Nappholz et al. | |
| 5,818,990 A | 10/1998 | Steijer et al. | |
| 5,827,195 A | 10/1998 | Lander | |
| 5,827,997 A | 10/1998 | Chung et al. | |
| 5,830,209 A | 11/1998 | Savage et al. | |
| 5,836,895 A | 11/1998 | Ramsey, III | |
| 5,861,012 A | 1/1999 | Stroebel | |
| 5,865,839 A | 2/1999 | Doorish | |
| 5,867,361 A | 2/1999 | Wolf et al. | |
| 5,868,664 A | 2/1999 | Speier et al. | |
| 5,869,412 A | 2/1999 | Yenni, Jr. et al. | |
| 5,870,272 A | 2/1999 | Seifried et al. | |
| 5,871,509 A | 2/1999 | Noren | |
| 5,871,512 A | 2/1999 | Hemming et al. | |
| 5,873,898 A | 2/1999 | Hemming et al. | |
| 5,882,108 A | 3/1999 | Fraizer | |
| 5,882,305 A | 3/1999 | Dumoulin et al. | 600/421 |
| 5,891,171 A | 4/1999 | Wickham | |
| 5,895,980 A | 4/1999 | Thompson | |
| 5,897,577 A | 4/1999 | Cinbis et al. | |
| 5,899,927 A | 5/1999 | Ecker et al. | |
| 5,902,326 A | 5/1999 | Lessar et al. | |
| 5,916,162 A | 6/1999 | Snelton et al. | |
| 5,916,237 A | 6/1999 | Schu | |
| 5,917,625 A | 6/1999 | Ogusu et al. | |
| 5,919,135 A | 7/1999 | Lemelson | |
| 5,928,145 A | 7/1999 | Ocali et al. | |
| 5,928,270 A | 7/1999 | Ramsey, III | |
| 5,928,570 A | 7/1999 | Reo | |
| 5,940,554 A | 8/1999 | Chang et al. | |
| 5,946,086 A | 8/1999 | Bruce | |
| 5,951,596 A | 9/1999 | Bellinger | 607/89 |
| 5,954,660 A | 9/1999 | Legay et al. | |
| 5,957,857 A | 9/1999 | Hartley | |

| | | |
|---|---|---|
| 5,963,034 A | 10/1999 | Mahapatra et al. |
| 5,963,690 A | 10/1999 | Cheng |
| 5,967,977 A | 10/1999 | Mullis et al. |
| 5,968,083 A | 10/1999 | Ciciarelli et al. |
| 5,973,779 A | 10/1999 | Ansari et al. |
| 5,973,906 A | 10/1999 | Stevenson et al. |
| 5,978,710 A | 11/1999 | Prutchi et al. |
| 5,982,961 A | 11/1999 | Pan et al. |
| 5,985,129 A | 11/1999 | Gough et al. |
| 5,987,995 A | 11/1999 | Sawatari et al. ............. 73/705 |
| 5,999,853 A | 12/1999 | Stoop et al. |
| 5,999,857 A | 12/1999 | Weijand et al. |
| 6,005,191 A | 12/1999 | Tzeng et al. |
| 6,011,994 A | 1/2000 | Kronberg |
| 6,013,376 A | 1/2000 | Yenni, Jr. |
| 6,016,448 A | 1/2000 | Busacker et al. |
| 6,016,477 A | 1/2000 | Ehnebuske et al. |
| 6,023,641 A | 2/2000 | Thompson |
| 6,024,738 A | 2/2000 | Daikuzono et al. |
| 6,026,316 A | 2/2000 | Kucharczyk |
| 6,029,086 A | 2/2000 | Kim et al. |
| 6,029,087 A | 2/2000 | Wohlgemuth |
| 6,031,710 A | 2/2000 | Wolf et al. |
| 6,036,639 A | 3/2000 | Allred, III et al. |
| 6,036,654 A | 3/2000 | Quinn et al. |
| 6,044,301 A | 3/2000 | Hartlaub et al. |
| 6,052,613 A | 4/2000 | Takaki |
| 6,052,614 A | 4/2000 | Morris, Sr. et al. |
| 6,052,623 A | 4/2000 | Fenner et al. |
| 6,055,455 A | 4/2000 | O'Phelan et al. |
| 6,056,415 A | 5/2000 | Allred, III et al. |
| 6,056,721 A | 5/2000 | Shulze |
| 6,064,906 A | 5/2000 | Langberg et al. |
| 6,066,096 A | 5/2000 | Smith et al. |
| 6,067,472 A | 5/2000 | Vonk et al. |
| 6,076,003 A | 6/2000 | Rogel |
| 6,080,829 A | 6/2000 | Tapsak et al. |
| 6,090,473 A | 7/2000 | Yoshikawa et al. |
| 6,090,728 A | 7/2000 | Yenni, Jr. et al. |
| 6,091,015 A | 7/2000 | del Valle et al. ............. 136/243 |
| 6,091,744 A | 7/2000 | Sorin et al. |
| 6,091,987 A | 7/2000 | Thompson |
| 6,101,973 A | 8/2000 | Stewart et al. |
| 6,118,910 A | 9/2000 | Chang |
| 6,119,031 A | 9/2000 | Crowley .................... 600/407 |
| 6,129,745 A | 10/2000 | Sun et al. |
| 6,134,003 A | 10/2000 | Tearney et al. |
| 6,134,478 A | 10/2000 | Spehr |
| 6,142,678 A | 11/2000 | Cheng |
| 6,144,205 A | 11/2000 | Souza et al. |
| 6,144,866 A | 11/2000 | Miesel et al. |
| 6,144,881 A | 11/2000 | Hemming et al. |
| 6,146,415 A | 11/2000 | Fitz |
| 6,148,222 A | 11/2000 | Ramsey, III |
| 6,148,229 A | 11/2000 | Morris, Sr. et al. |
| 6,149,313 A | 11/2000 | Giebel et al. |
| 6,163,724 A | 12/2000 | Hemming et al. |
| 6,166,806 A | 12/2000 | Tjin |
| 6,169,921 B1 | 1/2001 | Ken Knight et al. |
| 6,171,240 B1 | 1/2001 | Young et al. |
| 6,173,203 B1 | 1/2001 | Barkley et al. |
| 6,179,482 B1 | 1/2001 | Takizawa et al. |
| 6,188,926 B1 | 2/2001 | Vock |
| 6,192,261 B1 | 2/2001 | Gratton et al. |
| 6,198,968 B1 | 3/2001 | Prutchi et al. |
| 6,198,972 B1 | 3/2001 | Hartlaub et al. |
| 6,208,899 B1 | 3/2001 | Kroll |
| 6,216,041 B1 | 4/2001 | Tierney et al. |
| 6,223,083 B1 | 4/2001 | Rosar |
| 6,226,545 B1 | 5/2001 | Gilderdale |
| 6,230,060 B1 | 5/2001 | Mawhinney |
| 6,236,879 B1 | 5/2001 | Konings |
| 6,238,686 B1 | 5/2001 | Burrell et al. |
| 6,240,317 B1 | 5/2001 | Villaseca et al. |
| 6,245,020 B1 | 6/2001 | Moore et al. |
| 6,246,910 B1 | 6/2001 | Bonnet et al. |
| 6,247,474 B1 | 6/2001 | Greeninger et al. |
| 6,254,632 B1 | 7/2001 | Wu et al. |
| 6,256,537 B1 | 7/2001 | Stoop et al. |
| 6,256,541 B1 | 7/2001 | Heil et al. |
| 6,258,087 B1 | 7/2001 | Edwards et al. |
| 6,259,843 B1 | 7/2001 | Kondo |
| 6,259,954 B1 | 7/2001 | Conger et al. |
| 6,263,229 B1 | 7/2001 | Atalar et al. |
| 6,263,242 B1 | 7/2001 | Mika et al. |
| 6,266,555 B1 | 7/2001 | Werner et al. |
| 6,266,563 B1 | 7/2001 | Ken Knight et al. |
| 6,266,564 B1 | 7/2001 | Hill et al. |
| 6,266,566 B1 | 7/2001 | Nichols et al. |
| 6,270,457 B1 | 8/2001 | Bardy |
| 6,270,831 B2 | 8/2001 | Kumar et al. |
| 6,272,377 B1 | 8/2001 | Sweeney et al. |
| 6,272,380 B1 | 8/2001 | Warman et al. |
| 6,274,265 B1 | 8/2001 | Kraska et al. |
| 6,275,730 B1 | 8/2001 | Ken Knight et al. |
| 6,275,732 B1 | 8/2001 | Hsu et al. |
| 6,275,734 B1 | 8/2001 | McClure et al. |
| 6,277,078 B1 | 8/2001 | Porat et al. |
| 6,277,107 B1 | 8/2001 | Lurie et al. |
| 6,278,057 B1 | 8/2001 | Avellanet |
| 6,278,277 B1 | 8/2001 | Zeiger |
| 6,278,894 B1 | 8/2001 | Salo et al. |
| 6,278,897 B1 | 8/2001 | Rutten et al. |
| 6,296,654 B1 | 10/2001 | Ward |
| 6,317,633 B1 | 11/2001 | Jorgenson et al. |
| 6,367,984 B1 | 4/2002 | Stephenson et al. |
| 2002/0183796 A1 * | 12/2002 | Connelly |

OTHER PUBLICATIONS

Donald Fink; "Electronic Engineering," Electronic Engineers Handbook; 2nd edition, Mcgraw Hill; (1982); Section 14; pp. 29–45.

X Luo et al., "Electromagnetic Interference Shielding Using Continuous Carbon–Fiber Carbon–Matrix and PolymerMatrix Composites," Composites Part B: Engineering; (1999); pp. 227–231.

D.D.L. Chung, "Flexible Graphite for Gasketing, Absorption, Electromagnetic Interference Shielding, Vibration Damping, Electrochemical Applications, and Stress Sensing," Journal of Materials, Engineering and Performance; Apr. 2000; vol. 9 p. 161–163.

M. Konings et al., "Catheters and Guidewires in Inerventional MRI; Problems and Solutions," Medical Mundi; 45/1; Mar. (2001).

M. Konings; "Development of an MR–Safe Tracking Catheter with a Laser DrivenTip Coil,".

Ey Wong et al., "An Optical System for Wireless Detuning of Parallel Resonant Circuits" Journal of Magnetic Resonance Imaging; (2000); vol. 12, pp. 632–638.

Bernd Nowak; "Taking Advantage of Sophisticated Pacemaker Diagnostics," Excerpta Medica; (1999); pp. 172D–179D.

Jose A. Jogler et al., "Interaction of a Commercial Heart Rate Monitor With Implanted Pacemakers," Excerpta Medica; (1999); pp. 790–792.

J.A. Pomposo et al., "Polypyrrole–based Conducting Hot Melt Adhesives for EMI Shielding Applications," Elsevier; Synthetic Metals 104: (1999); pp. 107–111.

K. Grattan et al., "Fiber Optic Sensor Technology: An Overview," Elsevier; Sensors and Actuators 82: (2000);pp. 40–61.

L. Rippert et al., "Optical and Acoustic Damage Detection in Laminated CFRP Composite Materials," Elsevier; Composites Science and Technology 60; (2000); pp. 2713–2724.

C. Strandman et al., "A Production Process of Silicon Sensor Elements for a Fibre–Optic Pressure Sensor," Elsevier; Sensors and Actuators A63; (1997); pp. 69–74.

D. Howard et al., "A Single–Fringe Etalon Silicon Pressure Transducer," Elsevier; Sensors and Actuators 86; (2000); pp. 21–25.

Dan Haronian, "Displacement Sensing Using Geometrical Modulation in Reflection Mode (GM–RM) of Coupled Optical Waveguides," J. Micromech, Microeng., (UK), (1998); pp. 323–326.

H Ghafouri–Shiraz, "A Novel Distribued Feedback Laser Diode Structure foran Optical Wavelength Tunable Filter," Semicond. Sci. Technol. 12; (UK), (1997); pp. 1161–1165.

L. Kasarian, "A New Optical Fiber Multiplexer for Distortion–Free Light Transfer in Multichannel Fiber Optic Sensor Systems," Elsevier; Sensors and Actuators 84: (2000); pp. 250–258.

X. Yan et al., "Electric Field Controlled 2x2 Bypass Exchange Photorefractive Switch," IOP Publishing; (UK) (1998), pp. 383–386.

E. Piener et al., "A Micromachined Vibration Sensor Based on the Control of Power Transmitted Between Optical Fibres," Elsevier; Sensors and Actuators A65; (1998) pp. 23–29.

D. Sun et al., "High Performance Unidirectional Electrooptic Modulator Based On Polymeric Highly Multi–Mode Waveguides," Elsevier; Optics & Laser Technology 30; (1998); 481–489.

Engin Molva; "Microchip Lasers and Their Applications In Optical Microsystems," Elsevier; Optical Materials 11; (1999); pp. 289–299.

J. Linares et al., "Theory and Design of an Integrated Optical Sensor Based on Planar Waveguiding Lenses," Elsevier; Optics Communications 180; (2000); pp. 29–36.

O. Parriaux et al., "Coupling Gratings as Waveguide Functional Elements," IOP Publishing; Pure Appl. Opt. 5; (1996); pp. 453–469.

E T Enikov et al., "Three–Dimensional Microfabrication for a Multi–Degree of Freedom Capacitive Force Sensor Using Fibre–Chip Coupling" IOP Publishing; (UK); J. Micromechl. Microeng. 10;(2000) pp. 492–497.

J. Holm et al., "Through–Etched Silicon Carriers for Passive Alighnment of Optical Fibers to Surface–Active Optoelectronic Components" Elsevier; Sensors and Actuators 82; (2000) pp. 245–248.

M. Kimura et al., "Vibration Sensor Using Optical–Fiber Catilever with Bulb–Lens" Elsevier; Sensors and Actuators A66: (2000) pp. 178–183.

Y. Mao et al., "Three–Stage Wavelength Converter Based on Cross–Grain Modulation in Semiconductor Optical Amplifiers"Elsevier; Optics Communications 167; (1999) pp. 57–66.

X. Hu et al., "Dynamically Induced Irreversibility: Light Amplification and Quantum Noise Reduction in a V–Type Three–Level System" IOP Publishing; J. Opt. B: Quantum Semiclass. Opt. 2; (UK) (2000); pp. 570–575.

Y. Yim et al., "Lithium Niobate Integrated–Optic Voltage Sensorwith Variable Sensing Ranges" Elsevier; Optics Communications 152; Jul. 1, 1998; pp. 225–228.

C. Lee et al., "Electromagnetic Interference Shilding Efficiency of Polyaniline Mixtures and Multilayer Films" Elsevier; Synthetic Metals 102; (1999) pp. 1346–1349.

Marc Desmulliez, "Optoelectronics–VLSI System Integration Technological Challenges" Elsevier; Materials Science and Engineering B74;(2000) pp. 269–275.

J. Zook et al., "Fiber–optic Vibration Sensor Baed on Frequency Modulation of Light–Excited Oscillators" Elsevier; Sensors and Actuators 83; (2000); pp. 270–276.

M. Reta–Hernandez et al., "Attenuation of Low Frequency Magnetic Fields Using Active Shielding" Elsevier; Electric Power Systems Research 45; (1998); pp. 57–63.

C. Huang et al., "The EMI Shielding Effectiveness of PC/ABS/Nickel–Coated Carbon–Fibre Composites" Elsevier; European Polymer Journal 36; (2000) pp. 2727–2737.

M. Balucani et al., "Optical Link for DigitalTransmissions Using Porou Silicon Light Emitting Diode" Elsevier; Journal of Non–Crystalline Solids 266–269; (2000) pp. 1238–1240.

D. Egelman et al., "Calcium Dynamics in the Extracellular Space of Mammalian Nerual Tissue" Biophysical Journal; vol. 76; Apr. 1999; pp. 1856–1867.

M. Reta–Hernandez et al., "Attenuation of low frequency magnetic fields using active shielding" Elsevier; European Polymer Journal 36; (2000) pp. 1238–1240.

Biomedizinische Technik Band 35; Erganzungsband–1990; A Non–Magnetic, MR–Compatible Pacing Catheter for Clinical Application in Magnetocardiography; pp. 162–163.

Carlton F. Roos, B.A. and Frank E. Carroll, Jr. M.D..; Fiber–Optic Pressure Transducer for Use Near MR Maganetic Fields; RSNA 1985; one page.

Kenneth A. Wickersheim and Mei H. Sun; Fiberoptic Thermotmetry and its Applications; J. Microwave Power 1987; pp. 85–94.

Anastazia Jerewski et al.; Development of a MRI–Compatible Catheter for Pacing the Heart: Initial In Vitro and Vivo Results; ISMRM–1996; pp. 948–949.

Mark B. M. Hofman, Ph.D.; MRI–Compatible Cardiac Pacing Catheter; JMRI May/Jun. 1997; p. 612.

A. A. Damji et al.; RF Interference Suppression in a Cardiac Synchronization System Operating in a High Magnetic Field NMR Imaging System; Magnetic Resonance Imagan, vol. 6, pp. 637–640, 1988.

Frank G. Shellock, Ph.D. et al.; Burns Associated wit the use of Monitoring equipment during MR procedures; JMRI Jan./Feb. 1996; pp. 271–272.

J.A. Nyenhuis et al.; Heating near Implanted Medical Devices by the NRI RF–magnetic Field; IEEE Trans. Mag. Sep. 1999; four pages.

Frank G. Shellock, Ph.D.; eta l.; Cardiovascular Catheters and Accessories: Ex Vivo Testing of Ferromagnetism, Heating, and Artifacts Associated with MRI; JMRI Nov./Dec. 1998 vol. 8 #6; pp. 1338–1342.

J. Rod Gimbel et al.; Safe Performance of Magnetic Resonance; PACE, vol. 19 Jun. 1996; pp. 913–919.

National Library of Medicine; Pub Med; Pacing Clin Electrophysiol 1998 Jun.; 21(6):1336–9; Rapid Ventricular pacing in a pacemaker patient undergoing magnetic resonance imaging; p. 1.

National Libary of Medicine; Pub Med; Am Heart J 1997 Set; 134(3):467–73; Effects of maganetic resonance imaging on cardiac pacemakers and electrodes; pp. 1–2.

Adam Hilger; "Physics and Chemistry of Crystalline Lithium Niobate"; The Adam Hilger Series on Optics and Optoelectronics; A M Prokhorov and Yu S Kuz'minov; 4 pages.

* cited by examiner

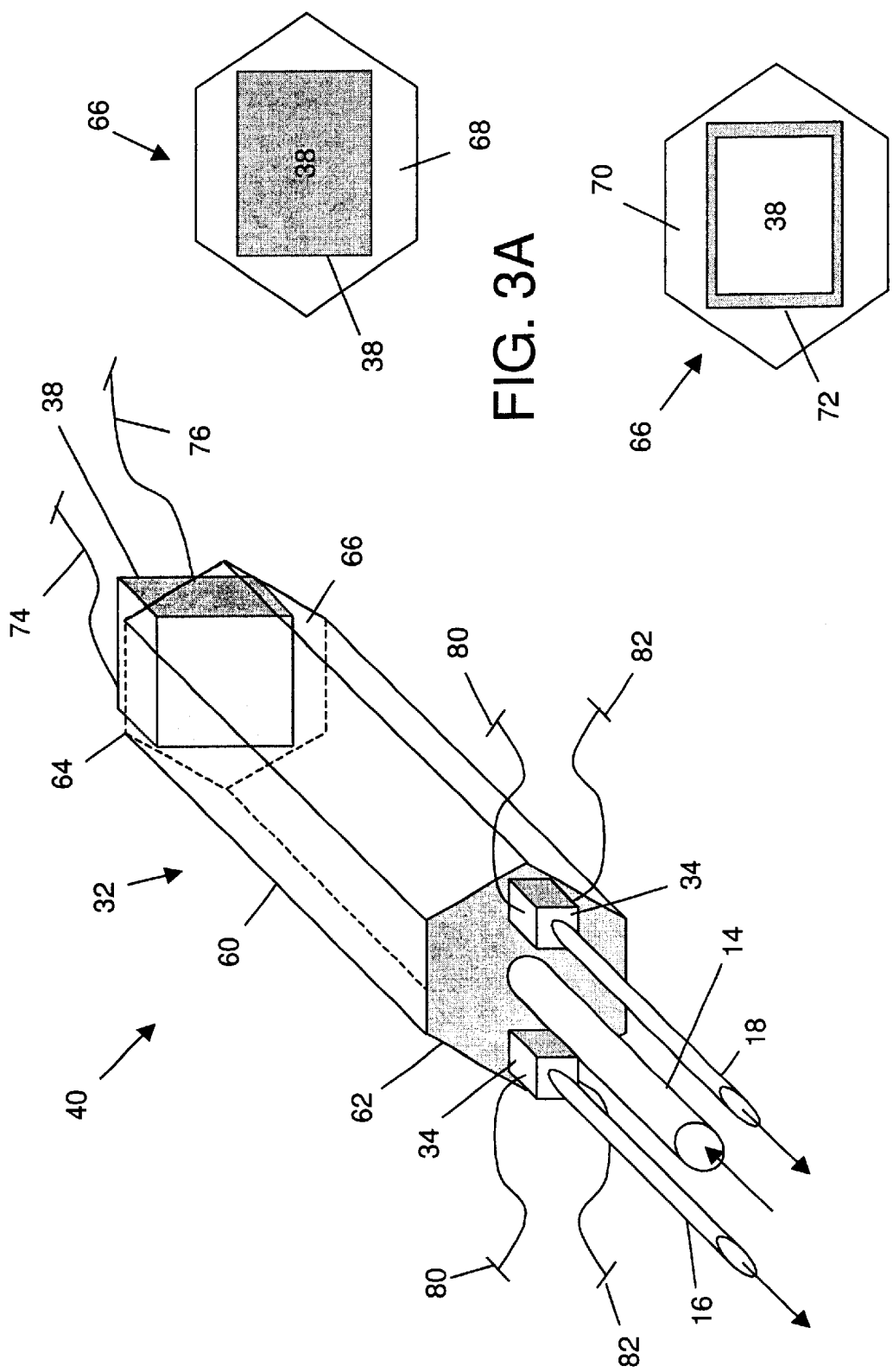

MRI-COMPATIBLE MEDICAL DEVICE WITH PASSIVE GENERATION OF OPTICAL SENSING SIGNALS

BACKGROUND OF THE INVENTION

1. Field of the Invention

The present invention relates to photonic pacemakers designed for compatibility with MRI diagnostic equipment, and to other opto-electric medical stimulation and sensing equipment. More particularly, the invention concerns an MRI-compatible medical device with passive generation of optical sensing signals.

2. Description of Prior Art

By way of background, MRI compatible pacemakers for both implantable and wearable use have been disclosed in copending application Ser. Nos. 09/864,944 and 09/865,049, both filed on May 24, 2001, and copending Ser. Nos. 09/885,867 and 09/885,868, both filed on Jun. 20,2001. In the aforementioned copending patent applications, whose contents are fully incorporated herein by this reference, the disclosed pacemakers feature photonic catheters carrying optical signals in lieu of metallic leads carrying electrical signals in order to avoid the dangers associated with MRI-generated electromagnetic fields. Electro-optical and opto-electrical transducers are used to convert between electrical and optical signals. In particular, a laser diode located in a main pacemaker enclosure at a proximal end of the photonic catheter is used to convert electrical pulse signals generated by a pulse generator into optical pulses. The optical pulses are carried over an optical conductor situated in the photonic catheter to a secondary housing at the distal end of the photonic catheter, where they are converted by a photo diode array into electrical pulses for cardiac stimulation.

Despite the advances in pacemaker MRI compatibility offered by the devices of the above-referenced copending applications, there remains a problem of how to provide physiological sensing capability in such devices. In a conventional pacemaker, there are direct electrical pathways between the power source (typically a lithium battery) and the circuitry responsible for generating stimulation and sensing signals. Because the circuitry has low power requirements, battery life can be prolonged for relatively long time periods. With a photonic pacemaker as contemplated by the above-referenced copending applications, the power requirements are greater due to the high current demands of the laser diodes used for optical signal generation, and the inefficiencies associated with opto-electrical and electro-optical conversion. Sensing signals are especially problematic. Most devices used to sense physiological conditions rely on electrical signals. These include "R" wave sensors for sensing electrical activity in the heart, partial oxygen (pO$_2$) sensors, temperature sensors, etc. Such electrical signals are very low in power (e.g., less than one milliwatt) and cannot be directly used to drive conventional electro-optical transducers, such as laser diodes or light emitting diodes. Instead, they need to be amplified or otherwise conditioned in order to boost their strength to a point where they can be converted into optical form. Only then can the sensing signals be transported over the photonic catheter to upstream sensing circuitry. It will thus be appreciated that a source of electrical power is required at the distal end of the photonic catheter. This poses a non-trivial design problem in the photonic medical equipment art.

SUMMARY OF THE INVENTION

The foregoing problem is solved and an advance in the art is provided by a novel system and method for passive optical sense signal generation in a photonic pacemaker or other opto-electric medical device. The system is adapted to operate at the distal end of an implantable photonic catheter having one or more optical conductors for conducting light energy in two directions between electronics at a proximal end of the catheter and electrical stimulation and sensing components at the catheter distal end. The latter may include pacing electrodes, sensing electrodes, partial oxygen sensors, temperature sensors, etc.

An optical unit receives a light input delivered from the catheter proximal end by one (or more) of the optical conductors. The optical unit directs a first portion of the light input as a first light output to an opto-electrical converter for conversion into electrical stimulation signals and directs a second portion of light input as a second light output to one or more optical modulators that modulate the second light output under applied electrical signals. An electrical circuit is connected to the device's sensing component(s). The electrical circuit generates electrical sense signals corresponding to one or more sensed physiological conditions and provides the signals to the optical modulator(s). This results in modulation of the second light output into optical sense signals that are transmitted over one or more of the catheter's optical pathways to the catheter proximal end.

In preferred implementations of the invention, the optical unit comprises a prismatic optical homogenizer having a first end adapted to receive the light input and a second end having a partially reflective coating thereon. The partially reflective coating allows the portion of the light input to pass as the first light output and reflects the second portion of the light input back to the first end as the second light output. The optical modulators can then be mounted on the first end of the optical homogenizer. The partially reflective coating can be formed as a partially reflective material covering all of the second end. Alternatively, it can be formed as a fully reflective material covering a peripheral portion of the second end while leaving uncovered a central portion of the second end for transmitting the second portion of the light input. The optical modulator can be formed from a crystalline material having electrically controllable optical properties. Exemplary materials include crystal structures selected from the group consisting of lithium niobate, indium phosphide and gallium arsenide. The electrical circuit is preferably adapted to condition a physiological sense signal generated via interaction with body tissue into the electrical sense signal. The electrical circuit is preferably also adapted to obtain electrical power from the transmitted light output. Additionally, the electrical circuit may be adapted to convert the electrical sense signal form analog to digital form.

The invention further contemplates, respectively, a photonic pacemaker and an opto-electric medical stimulation system having the above-summarized optical sense signal generating functionality therein.

BRIEF DESCRIPTION OF THE DRAWINGS

The foregoing and other features and advantages of the invention will be apparent from the following more particular description of preferred embodiments of the invention, as illustrated in the accompanying Drawings in which:

FIG. 2 is a perspective view of an optical assembly forming part of the optical sense signal generation system of FIG. 1;

FIGS. 3A and 3B are cross-sectional views taken along line 3—3 in FIG. 2 showing alternative partial light reflecting structures of an optical homogenizer constructed in accordance with the invention;

DETAILED DESCRIPTION OF PREFERRED EMBODIMENTS

Figure 1:
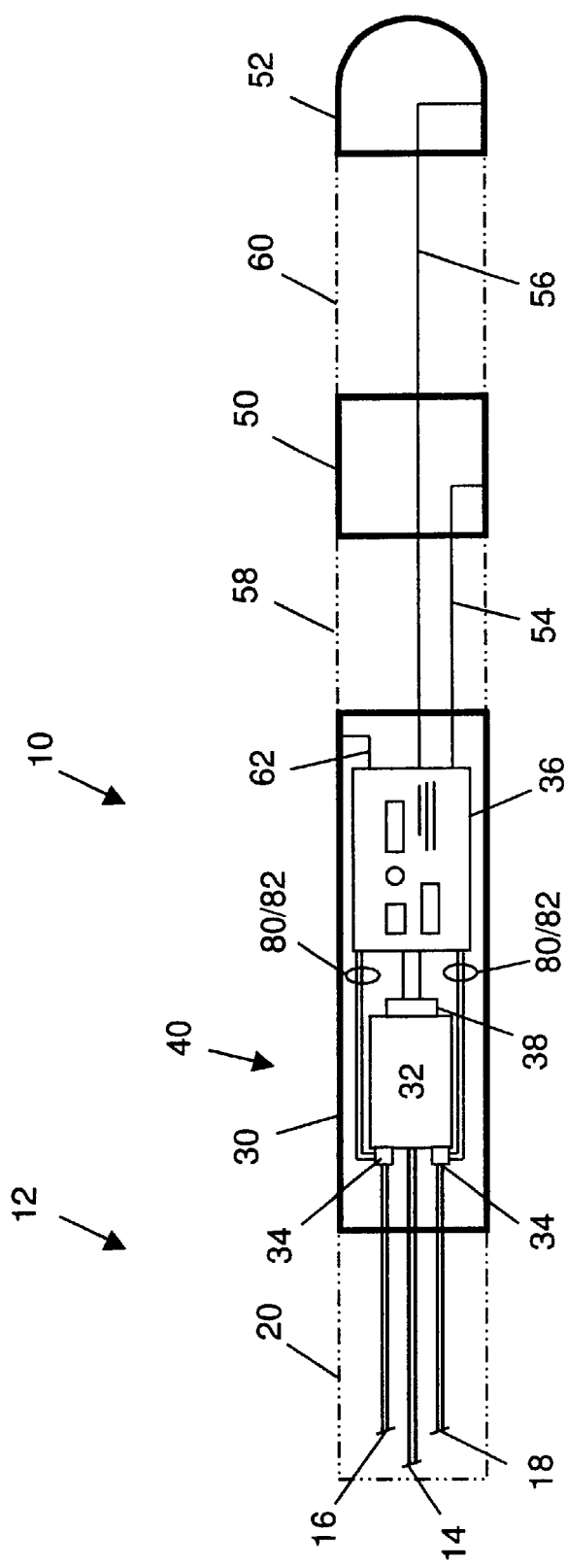
FIG. 1 is a partial diagrammatic side view showing the distal end of a photonic catheter that incorporates an optical sense signal generation system in accordance with the invention.

Turning now to the Drawings wherein like reference numerals signify like elements in all of the several views, FIG. 1 illustrates a passive optical sense signal generation system 10 located at the distal end of an implantable photonic catheter 12. As will be described in more detail below, the photonic catheter 12 is operatively connected to a photonic pacemaker or other opto-electric medical stimulation/sensing device (not shown in FIG. 1). Such devices may include, but are not limited to, optically driven defibrillators, neural stimulators, and other medical equipment designed to perform body tissue stimulation and/or sensing functions using optical transmission signals.

The catheter 12 is preferably has a diameter no larger than 5 millimeters, which should be suitable for cardiac implantation. For neuro-stimulation applications, the catheter 12 should be smaller. The catheter 12 has at least one, and preferably several optical conductors (such as optical glass fibers) for conducting light energy in two directions between electronics at a proximal end of the catheter and electrical stimulation and sensing components at the catheter's distal end. The electronics at the catheter proximal end may be implanted within a patient's body or may be external to the body. The catheter distal end comprises optical and optoelectronic components, electronic circuitry and electrodes that provide electrical interfaces to body tissue.

Three optical conductors 14, 16 and 18 are shown by way of example in FIG. 1. The optical conductor 14 is adapted to carry optical signals in a downstream direction from the catheter proximal end to the catheter distal end. The optical conductors 16 and 18 are adapted to carry optical signals in an upstream direction from the catheter distal end to the catheter proximal end. All of the optical conductors are encased in a flexible sheath 20 that is made from a material that is biocompatible and non-electrically conductive, such as silicone rubber.

The components of the sense signal generation system 10 are contained within a housing 30 that is preferably cylindrical and of the same diameter as the sheath 20. The principal components of the sense signal generation system 10 are an optical unit 32, one or more optical modulators 34 (two are shown), and an electronic circuit assembly 36. The optical unit 32 and the optical modulators 34 are preferably combined with an opto-electrical converter 38 (e.g., a photodiode array) to form an integrated optical detector/modulator assembly 40. The optical detector/modulator assembly 40 provides an interface between the optical conductors 14–18 and the electronic circuit assembly 36. The latter further provides an interface to plural physiologic interaction components designed to interact with implanted body tissue in a medically significant manner by imparting stimulating electrical signals, by sensing physiological activity, or both. A ring electrode 50 and a tip electrode 52 are depicted by way of example. Both of these physiologic electrodes are electrically connected to the electronic circuit assembly 36 via respective electrical leads 54 and 56. The electrodes 50 and 52 provide connections to body tissue in order to support electrical stimulation and monitoring functions. For example, the electrodes 50/52 could be used to deliver pacing, defibrillation or other stimulation pulses. In addition, or in the alternative, the electrodes 50/52 could be used for sensing cardiac R waves or other physiological electrical activity. The electrodes 50 and 52 are made from a suitable electrically conductive, bio-compatible material, such as platinum or an alloy thereof. The ring electrode 50 is preferably cylindrical in shape while the tip electrode 52 is generally bullet shaped to facilitate tissue implantation. Both electrodes can be formed with hollow cavities that are filled with a biocompatible non-electrically conductive material, such as the material forming the catheter sheath 20. The same material can also be used to form a pair of short cylindrical stub members 58 and 60. The stub member 58 separates and electrically isolates the ring electrode 50 from the housing 30. The stub member 60 separates and electrically isolates the tip electrode 52 from the ring electrode 50.

Although not shown, it will be appreciated that other physiologic interaction components could be provided at the distal end of the catheter 12. Such components include partial oxygen sensors, temperature sensors, and other devices. Note that the housing 30 may itself be a physiologic electrode for delivering and/or sensing electrical signals. The housing 30 would then be preferably made from the same material as the electrodes 50 and 52. An electrical lead 62 would connect the housing 30 to the electronic circuit assembly 36. Note that the various components within the housing 30 should be hermetically sealed to protect the components from body fluids. This can be done in a variety of ways. For example, after the components are situated in the housing 30, and the housing interior can be charged with a bio-compatible insulative material, such as the material used to form the catheter sheath 30 and the stubs 58 and 60.

Before turning to the construction details of the sense signal generation system 10, it should be further mentioned that the housing 30 is not be the only structure that can be used to house the various components of the system. Persons skilled in the art will appreciate that alternative designs could be readily implemented in which the components of the sense signal generation system 10 are situated within the ring electrode 50, or within the tip electrode 52, or possibly distributed across plural housing and/or electrodes.

Turning now to FIGS. 2 and 3A/3B, the design of the optical detector/modulator assembly 40 will now be described. As stated above, the main components of this assembly are the optical unit 32, one or more optical modulators 34, and an opto-electrical converter 38. The optical unit 32 is adapted to receive a light input from the distal end of the optical conductor 14. The optical unit 32 directs a first portion of the light input as a first light output to the opto-electrical converter 38 for conversion into electrical stimulation signals. The optical unit 32 directs a second portion of light input as a second light output to the optical modulators 34, which modulate the second light output under applied electrical signals provided by the electronic circuit 36. The optical unit thus functions in the manner of an optical splitter whose job is to direct one portion of the light input to the opto-electrical converter 38 while directing (e.g., by partial reflection) another portion of the light input to the optical modulators 34.

The foregoing functionality of the optical unit can be provided in a variety of ways, using a variety of optical unit configurations. FIG. 2 illustrates one possible implementation in which the optical unit 32 is constructed as an optical homogenizer 60. The optical homogenizer 60 has a first end 62 adapted to mount or otherwise functionally interact with the distal end of the optical conductor 14, so as to thereby receive a light input therefrom, and to mount the optical modulators 34. The optical homogenizer 60 has a second end 64 that is associated with a partial light reflecting structure 66, and is also adapted to mount the opto-electrical converter 38. In preferred implementations of the invention, the optical homogenizer 60 is a prismatic optical homogenizer constructed from glass or other suitable material. Such devices are generally known in the optical communications art. However, a smaller scale device is required for implantable medical use. For example, to be fully implantable for cardiac applications, the optical homogenizer 60 should be preferably no wider than 1–3 millimeters and no longer than about 3–10 millimeters. Neuro-stimulation applications will typically require smaller dimensions. The optical homogenizer 60 of FIG. 2 is a hexagonal prism. Other configurations, including cylinders, could also be used.

The design of the optical homogenizer 60, including the partial reflector structure 66, preferably maximizes the energy transfer of the first light output provided to the opto-electrical converter 38. To that end, the partial light reflecting structure 66 can be implemented in a variety of ways, but is preferably formed as a coating on the back face of the optical homogenizer's second end 64. Different coating configurations and materials can be used. For example, as shown in FIG. 3A, a partially reflective coating material 68 could be applied so as to cover substantially all of the second end 64. All areas of the coating 68 would pass the first light output to the opto-electrical converter while reflecting the second light output to the optical modulators 34. Alternatively, as shown in FIG. 3B, a fully reflective coating material 70 could be applied to only a peripheral portion of the second end 64 so as to leave uncovered a central portion 72 of the second end. The open central portion 72 would pass a central portion of the light input as the first light output to the opto-electrical converter 38. The peripheral area of the second end 64 having the fully reflective material 70 applied thereto would then reflect a peripheral portion of the light input as the second light output to the optical modulators 34. Note that the coating materials 68 and 70 can be applied to the second end 64 using conventional techniques.

The optical modulators 34 are mounted on the front end 62 of the optical homogenizer 60. Each optical modulator 34 also connects to, or otherwise functionally interacts with, a respective one of the optical conductors 16 and 18. Each optical modulator 34 further has a pair of electrical leads 80 and 82 respectively connected to opposing faces thereof. As described in more detail below, the electrical lead pairs 80/82 are connected to a modulating element of the electronic circuit 36, so that the electronic circuit is able to modulate light passing through the optical modulators. In particular, the electrical signals from the electronic circuit 36 serve to modulate the intensity of the light passed through the optical modulators 34 in proportion to the applied electrical signals. With this arrangement, the modulators 34 are positioned to receive the second light output provided by the partial light reflecting structure 66, and to feed the second light output with an applied modulation signal into the optical conductors 16 and 18 for transport to the proximal end of the catheter 12.

The optical modulators can be formed in conventional fashion from a crystalline material having electrically controllable optical properties. Exemplary materials include crystal structures selected from the group consisting of lithium niobate, indium phosphide and gallium arsenide, as is well known in the optical communications art. The physics of a high voltage version of a lithium niobate optical modulator are discussed in A. M. Prokhorov et al., "Physics and Chemistry of Crystalline Lithium Niobate, (1990). In addition, a lithium niobate modulator is described that is five millimeters in length (between the faces that mount the electrical connections) and two millimeters in width (in the direction of the light transmitted through the optical modulator). This prior art optical modulator uses a control voltage of up to 5000 volts. For the optical modulators 34 described herein, a much lower control voltage is used. Thus, a much thinner optical modulator element, perhaps only a millimeter or less on each side, will be used to permit use of a control voltage of a few volts. Persons skilled in the art will recognize that other light modulator materials, such as indium phosphide or gallium arsenide, could be used with corresponding different control voltages.

As stated above, the opto-electrical converter 38 is mounted at the second end 64 of the optical homogenizer 60. The purpose of the opto-electrical converter 38 is to convert the incident light energy into electrical energy for physiological stimulation and to power the co-located electronic circuit 36. The opto-electrical transducer 38 may be constructed in a variety of ways, but is preferably implemented as an array of six series-connected photo diodes to develop the required photovoltaic output. The electrical output of the opto-electric converter 38 is connected to the physiologic electrodes 50, 52 and 60 of FIG. 1 by way of the electronic circuit 36. A pair of electrical leads 74 and 76 connect the opto-electrical converter 38 to the electrical circuit 36.

The operation of the optical detector/modulator assembly 40 depicted in FIG. 2 may be summarized as follows: Light energy from a source at the proximal end of the catheter 12 enters the first end 62 of the optical homogenizer 60 from the optical conductor 14 and is dispersed within the optical homogenizer. The optical homogenizer 60 is constructed in such a manner (by way of the partial light reflecting structure 66) as to transmit the bulk of the light input to the opto-electrical converter 38 while reflecting a small amount (e.g., less than 10%) of the incident light energy from its second end 64 back to its first end 62, where the optical modulators 34 are located. The reflected light energy will be passed through the optical modulators 34, modulated by the electronic circuit 36, and coupled into the optical conductors 16 and 18 to provide optical sense signals back to the electronics at the proximal end of the catheter 12.

Figure 4:
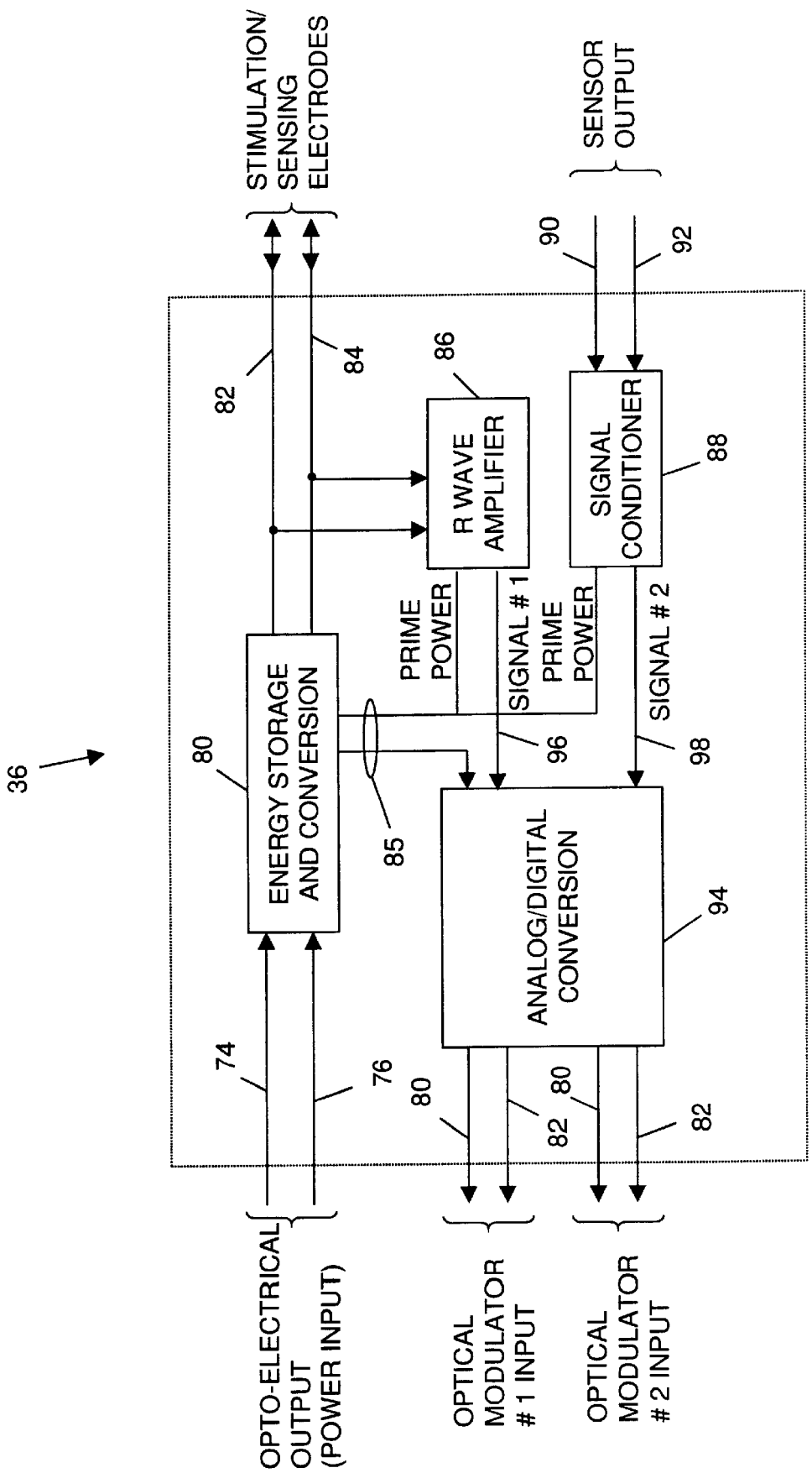
FIG. 4 is a functional block diagram of an electronic circuit assembly forming part of the optical sense signal generation system of FIG. 1.

Turning now to FIG. 4, the electronic circuit 36 of FIG. 1 is shown in more detail. This circuit performs several functions, including (1) providing electrical stimulation pulses to all electrodes performing a medical stimulation function, (2) amplifying or otherwise conditioning all physiological inputs received from sensing electrodes and other sensing components into electrical sense signals, and (3) optionally converting the electrical sense signals from analog to digital form for modulating the optical modulators 34. The electronic circuit 36 receives electrical power in the form of electrical pulses from the opto-electrical converter 38, by way of the electrical leads 74 and 76. A typical pulse would last about 1–10 milliseconds and develop a voltage potential of about 3–9 volts at a current level of about 4 milliamperes. This would produce a pulse power level of about 16 milliwatts, which would be sufficient for a medical stimulation function such as cardiac pacing. The pulses are delivered to an energy storage and conversion unit 80 whose function is to divert a portion of the electrical energy as power for other components of the electronic circuit 36, while coupling the bulk of the electrical energy to the stimulation electrodes via the electrical pathways 82 and 84. The energy storage and conversion unit 80 can be implemented using a conventional charge pump circuit that rectifies and stores the input electrical pulses using one or more capacitors. The diverted electrical power is provided to electrical power bus elements 85.

The electronic circuit 36 also includes an R wave amplifier 86 that is adapted to receive physiological sense signals from sensing electrode implanted in a patient's heart. The R wave amplifier 86 connects to the sensing electrodes via electrical pathways 82 and 84. It receives primary power from the power bus 85. Note that the sensing electrodes could be the electrodes 50 and 52 of FIG. 2, in which case the electrical pathways 83 and 84 would respectively comprise the electrical leads 54 and 56. The R wave amplifier 86 converts the heart's R wave pulse signals into electrical sense signals that are of sufficient power to modulate the optical modulators 34. The R wave amplifier can be implemented using any suitable low power amplification circuit designed for operation in the sub-milliwatt range.

If additional sensing functions are to be performed, other signal conditioning units may be provided and connected to accept inputs from other sensors. FIG. 4 shows one such signal conditioning unit 88 receiving physiological sense signals via a pair of electrical pathways 90 and 92. The signal conditioning unit 88 could be an amplifier or any other circuit adapted to scale a physiological sense signal generated via interaction with body tissue to an electrical sense signal of sufficient power to modulate the optical modulators 34. It could be connected to a desired sensor type, including partial oxygen sensors, temperature sensors, etc. Primary power is provided to the signal conditioning unit 88 via the power bus 86.

The electronic circuit 36 may additionally include an analog-to-digital (A/D) conversion circuit 94 for converting the electrical sense signals generated by the R wave amplifier 86 and the signal conditioning circuit 88 from analog to digital form. The A/D conversion circuit 94 receives power over the power bus 86. It receives analog sense signal inputs from R wave amplifier 86 and the signal conditioning unit 88 over respective electrical pathways 96 and 98. The digital outputs of the A/D conversion circuit 94 delivers digital outputs to the optical modulators 34 via the electrical pathways 80 and 82. The digital outputs provided by the A/D conversion circuit 94 are serial outputs. A conventional voltage-to-frequency (V/F) counter circuit may be used to implement the A/D conversion circuit 94. As is well known, such circuits produce a pulsitile output at a frequency that is based on the voltage level of the input analog signal.

Figure 5:
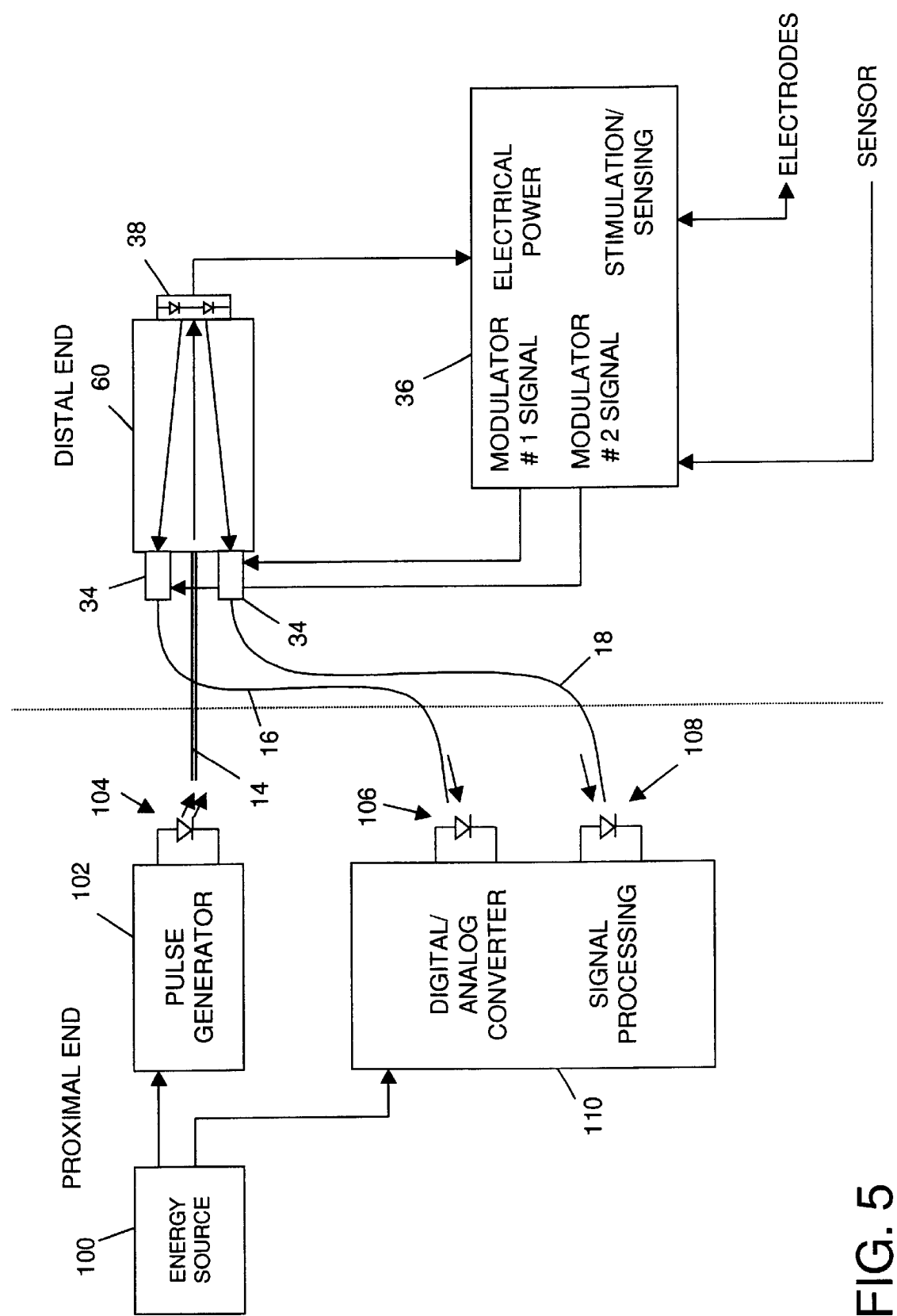
FIG. 5 is a functional block diagram showing the interconnection of electronic and optical circuitry in an optoelectric medical device incorporating a sense signal generation system in accordance with the invention.

Turning now to FIG. 5, the components of the optical sense signal generator 10 are shown in diagrammatic form at the distal end of the catheter 12. FIG. 5 also shows exemplary electronic circuit and optical components that might be found at the proximal end of the catheter 12. At the proximal end of the catheter 12, a prime energy source 100, such as a battery, provides prime power for the circuitry at the proximal end of the opto-electric medical device being implemented. The proximal end also includes a pulse generator circuit 102 to control and drive an electro-optical converter, such as a laser diode 104, which converts the applied electrical energy to light energy. The laser diode 104 will preferably be operated in a pulsed mode to minimize energy dissipation and to control physiological stimulation when required. The laser diode output energy is coupled to the optical conductor 14 and conducted to the distal end of the catheter 12.

At the distal end of the catheter 12, the light energy delivered by the optical conductor 14 is applied to the optical homogenizer 60. The optical homogenizer 60 couples the bulk of the incident light input into the opto-electrical converter 38. Here, the light is converted to electrical energy to power the electronic circuit 36 and provide physiological stimulation, as previously stated. The remainder of the light input is reflected by the partial light reflecting structure 66 back to the optical modulators 34. Electrical input signals from the electrodes and sensors at the distal end of the catheter 12 are amplified or conditioned and converted to digital pulse signals that modulate the optical modulators 34. This varies the light intensity passed through to the optical conductors 16 and 18 in proportion to the monitored physiological parameters, thereby providing encoded optical sense signals.

Back at the proximal end of the catheter 12, the modulated light energy carried on the optical conductors 16 and 18 from the distal end of the catheter is coupled to opto-electrical converters 106 and 108 to convert the optical sense signals to electrical sense signals. The electrical sense signals are provided to an electronic circuit assembly 110 comprising a digital-to-analog (D/A) converter and a signal processing circuit. The D/A converter converts the digital electrical sense signals to analog form and the signal processing circuit interprets the converted analog signals to recover the physiological parameters. The latter can then be used for any desired purpose, such as to affect the operation of the pulse generator 102 to provide a desired therapeutic effect.

Figure 6:
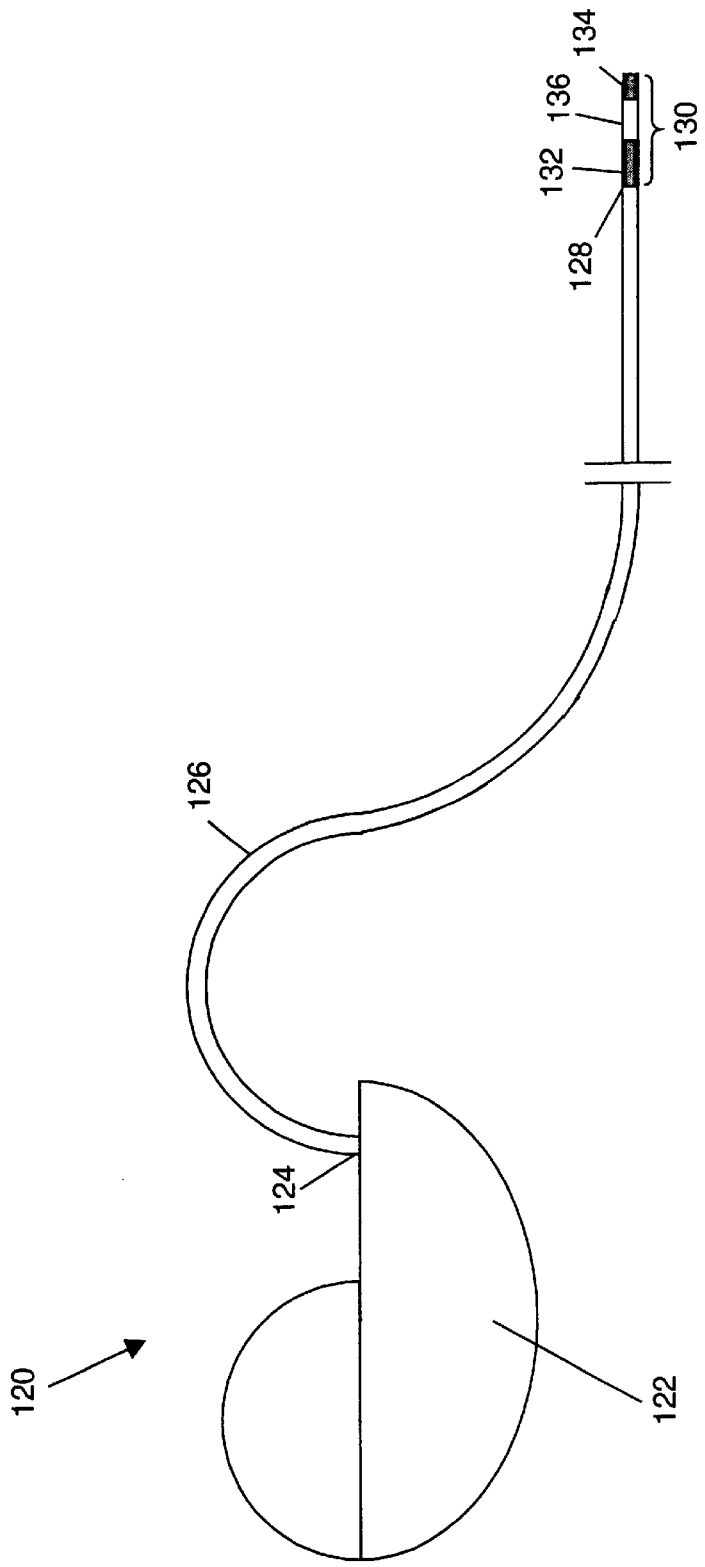
FIG. 6 is a diagrammatic view of an implantable pacemaker in accordance with the invention.
Figure 7:
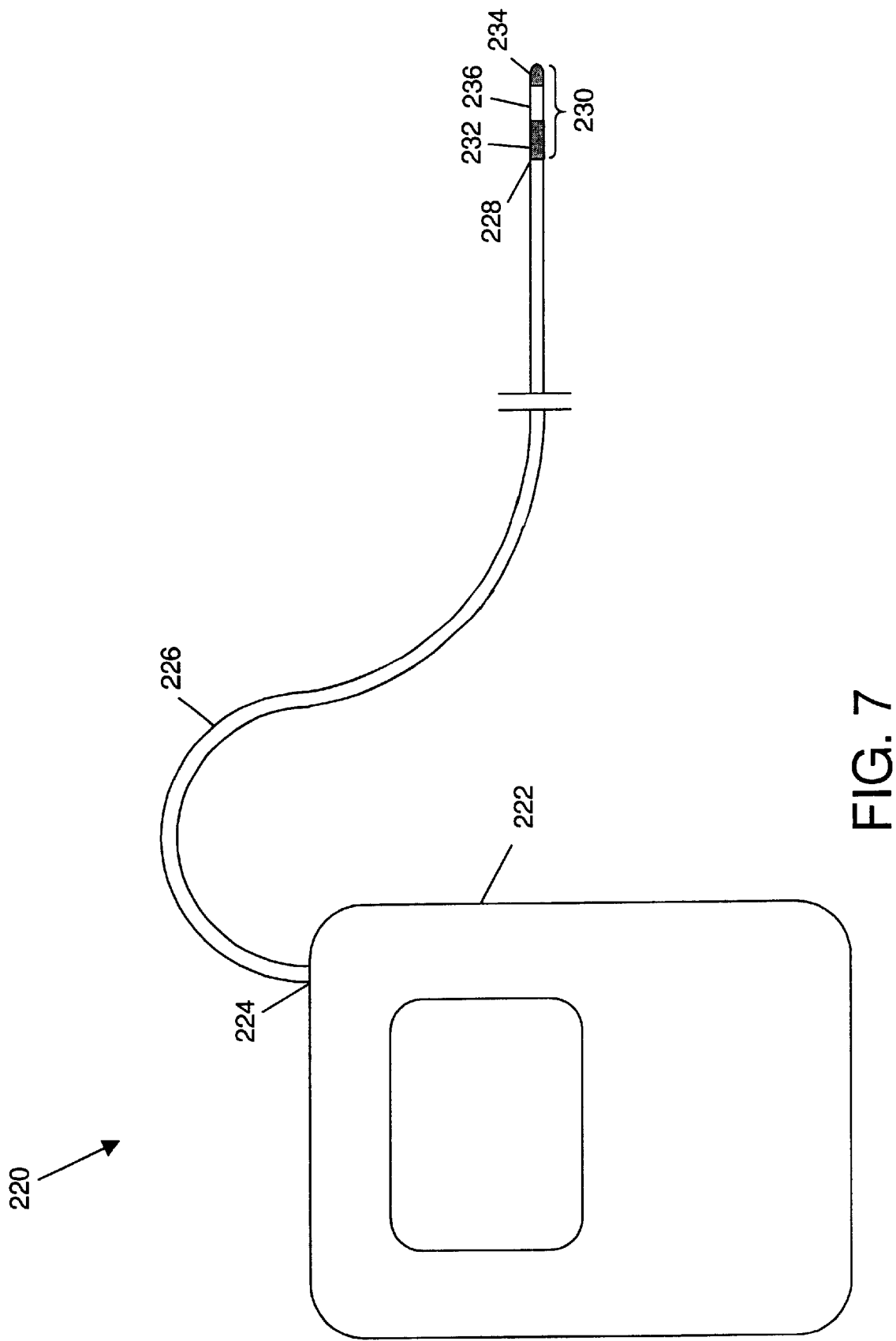
FIG. 7 is a diagrammatic view of a wearable pacemaker in accordance with the invention.

Turning now to FIGS. 6 and 7, two exemplary embodiments of the invention are shown in which the optical sense signal generation system 10 is respectively incorporated in an implantable photonic pacemaker and a wearable photonic pacemaker. FIGS. 6 and 7 further illustrate the use of two electrodes in which the ring electrode is used to house the system 10.

In FIG. 6, an implantable photonic pacemaker 120 includes an implantable housing 122 that preferably contains the proximal end circuit components shown in FIG. 5. The housing 122 mounts the proximal end 124 of a photonic catheter 126 that can be constructed in the same way as the catheter 12 of FIG. 1. At the distal end 128 of the catheter 126 is a tip/ring electrode termination pair 130 comprising a ring electrode 132 and a tip electrode 134 separated by a short insulative stub 136. The ring electrode 132 forms a housing that contains the various electrical and optical components that provide the optical sense signal generation system 10.

In FIG. 7, a wearable pacemaker 220 includes a wearable housing 222 that preferably contains the proximal end circuit components shown in FIG. 5. The housing 222 mounts the proximal end 224 of a photonic catheter 226 that can be constructed in the same way as the catheter 12 of FIG. 1. At the distal end 228 of the catheter 226 is a tip/ring electrode termination pair 230 comprising a ring electrode 232 and a tip electrode 234 separated by a short insulative stub 236. The ring electrode 232 forms a housing that contains the various electrical and optical components that provide the optical sense signal generation system 10.

Accordingly, a system and method for optical sense signal generation been disclosed. As described in detail above, we teach an optical diverter at the distal end of a photonic catheter that diverts a small portion of light energy delivered from the proximal end of the catheter back up one or more optical conductors. One or more optical modulators is provided in the path of the diverted light. The optical modulators modulate the intensity of the diverted light in accordance with one or more physiological variables such as, for example, R wave electrocardiographic activity. While various embodiments of the invention have been shown and described, it should be apparent that many variations and alternative embodiments could be implemented in accordance with the invention. It is understood, therefore, that the invention is not to be in any way limited except in accordance with the spirit of the appended claims and their equivalents.

We claim:

1. An optical sense signal generator for photonic pacemakers and other opto-electric medical stimulation equipment and adapted to operate at the distal end of an implantable photonic catheter having one or more optical conductors for conducting light energy in two directions between electronics at a proximal end of the catheter and electrical stimulation and sensing components at the catheter distal end, said optical sense signal generator, comprising:
   an optical unit adapted to receive a light input delivered from said catheter proximal end by one of said optical conductors and to transmit a first portion of said light input as a transmitted light output to an opto-electrical converter for conversion into electrical stimulation signals while diverting a second portion of said light input as a diverted light output;
   an optical modulator positioned to receive said diverted light output and adapted to modulate said diverted light output under an applied electrical signal;
   an electrical circuit in said sense signal generator, said electrical circuit being connected to an electrical sensing component at said catheter distal end and adapted to generate an electrical sense signal corresponding to a physiological condition to be sensed by said sensing component; and
   said electrical circuit being connected to provide said electrical sense signal to said optical modulator in order to modulate said diverted light output into a sensing optical signal;
   said optical unit being an optical homogenizer.

2. The optical sense signal generator as claimed in claim 1, wherein said optical homogenizer is a prismatic optical homogenizer having a first end adapted to receive said light input and a second end having a partially reflective coating thereon for reflecting said second portion of said light input to said first end.

3. The optical sense signal generator as claimed in claim 2, wherein said partially reflective coating comprises a partially reflective material covering all of said second end.

4. The optical sense signal generator as claimed in claim 2, wherein said partially reflective coating comprises a fully reflective material covering a peripheral portion of said second end while leaving uncovered a central portion of said second end for transmitting said second portion of said light input.

5. The optical sense signal generator as claimed in claim 1, wherein said electrical circuit comprises means for conditioning a physiological sense signal generated via interaction of said sensing component with body tissue into said electrical sense signal.

6. The optical sense signal generator as claimed in claim 1, wherein said electrical circuit comprises means for obtaining electrical power from said transmitted light output.

7. An optical sense signal generator for photonic pacemakers and other opto-electric medical stimulation equipment and adapted to operate at the distal end of an implantable photonic catheter having one or more optical conductors for conducting light energy in two directions between electronics at a proximal end of the catheter and electrical stimulation and sensing components at the catheter distal end, said optical sense signal generator, comprising:
   an optical unit adapted to receive a light input delivered from said catheter proximal end by one of said optical conductors and to transmit a first portion of said light input as a transmitted light output to an opto-electrical converter for conversion into electrical stimulation signals while diverting a second portion of said light input as a diverted light output;
   an optical modulator positioned to receive said diverted light output and adapted to modulate said diverted light output under an applied electrical signal;
   an electrical circuit in said sense signal generator, said electrical circuit being connected to an electrical sensing component at said catheter distal end and adapted to generate an electrical sense signal corresponding to a physiological condition to be sensed by said sensing component; and
   said electrical circuit being connected to provide said electrical sense signal to said optical modulator in order to modulate said diverted light output into a sensing optical signal;
   said optical modulator being composed of a crystalline material having electrically controllable optical properties.

8. The optical sense signal generator as claimed in claim 7, wherein said crystalline material is selected from the group consisting of lithium niobate, indium phosphide and gallium arsenide.

9. An optical sense signal generator for photonic pacemakers and other opto-electric medical stimulation equipment and adapted to operate at the distal end of an implantable photonic catheter having one or more optical conductors for conducting light energy in two directions between electronics at a proximal end of the catheter and electrical stimulation and sensing components at the catheter distal end, said optical sense signal generator, comprising:
   an optical unit adapted to receive a light input delivered from said catheter proximal end by one of said optical conductors and to transmit a first portion of said light input as a transmitted light output to an opto-electrical converter for conversion into electrical stimulation signals while diverting a second portion of said light input as a diverted light output;
   an optical modulator positioned to receive said diverted light output and adapted to modulate said diverted light output under an applied electrical signal;
   an electrical circuit in said sense signal generator, said electrical circuit being connected to an electrical sensing component at said catheter distal end and adapted to generate an electrical sense signal corresponding to a physiological condition to be sensed by said sensing component; and
   said electrical circuit being connected to provide said electrical sense signal to said optical modulator in order to modulate said diverted light output into a sensing optical signal;

said electrical circuit including means for converting said electrical sense signal from analog to digital form.

10. A photonic pacemaker having a photonic catheter containing one or more optical conductors for conducting light energy in two directions between electronics at a proximal end of said catheter and electrical stimulation and sensing components at a distal end of said catheter, comprising:

an optical sense signal generator located at said catheter distal end;

an optical unit in said sense signal generator adapted to receive a light input delivered from said catheter proximal end by one of said optical conductors and to transmit a first portion of said light input as a transmitted light output to an opto-electrical converter for conversion into electrical stimulation signals while diverting a second portion of said light input as a diverted light output;

an optical modulator in said sense signal generator positioned to receive said diverted light output and adapted to modulate said diverted light output under an applied electrical signal;

an electrical circuit in said sense signal generator, said electrical circuit being connected to an electrical sensing component at said catheter distal end and adapted to generate an electrical sense signal corresponding to a physiological condition to be sensed by said sensing component; and said electrical circuit being connected to provide said electrical sense signal to said optical modulator in order to modulate said diverted light output into a sensing optical signal;

said optical unit being an optical homogenizer.

11. The photonic pacemaker as claimed in claim 10, wherein said optical unit is a prismatic optical homogenizer having a first end adapted to receive said light input and a second end having a partially reflective coating thereon for reflecting said second portion of said light input to said first end.

12. The photonic pacemaker as claimed in claim 11, wherein said partially reflective coating comprises a partially reflective material covering all of said second end.

13. The photonic pacemaker as claimed in claim 11, wherein said partially reflective coating comprises a fully reflective material covering a peripheral portion of said second end while leaving uncovered a central portion of said second end for transmitting said second portion of said light input.

14. The photonic pacemaker as claimed in claim 10, wherein said electrical circuit comprises means for conditioning a physiological sense signal generated via interaction of said sensing component with body tissue into said electrical sense signal.

15. The photonic pacemaker as claimed in claim 10, wherein said electrical circuit comprises means for obtaining electrical power from said transmitted light output.

16. A photonic pacemaker having a photonic catheter containing one or more optical conductors for conducting light energy in two directions between electronics at a proximal end of said catheter and electrical stimulation and sensing components at a distal end of said catheter, comprising:

an optical sense signal generator located at said catheter distal end;

an optical unit in said sense signal generator adapted to receive a light input delivered from said catheter proximal end by one of said optical conductors and to transmit a first portion of said light input as a transmitted light output to an opto-electrical converter for conversion into electrical stimulation signals while diverting a second portion of said light input as a diverted light output;

an optical modulator in said sense signal generator positioned to receive said diverted light output and adapted to modulate said diverted light output under an applied electrical signal;

an electrical circuit in said sense signal generator, said electrical circuit being connected to an electrical sensing component at said catheter distal end and adapted to generate an electrical sense signal corresponding to a physiological condition to be sensed by said sensing component; and said electrical circuit being connected to provide said electrical sense signal to said optical modulator in order to modulate said diverted light output into a sensing optical signal;

said optical modulator being composed of a crystalline material having electrically controllable optical properties.

17. The photonic pacemaker as claimed in claim 16, wherein said crystalline material is selected from the group consisting of lithium niobate, indium phosphide and gallium arsenide.

18. A photonic pacemaker having a photonic catheter containing one or more optical conductors for conducting light energy in two directions between electronics at a proximal end of said catheter and electrical stimulation and sensing components at a distal end of said catheter, comprising:

an optical sense signal generator located at said catheter distal end;

an optical unit in said sense signal generator adapted to receive a light input delivered from said catheter proximal end by one of said optical conductors and to transmit a first portion of said light input as a transmitted light output to an opto-electrical converter for conversion into electrical stimulation signals while diverting a second portion of said light input as a diverted light output;

an optical modulator in said sense signal generator positioned to receive said diverted light output and adapted to modulate said diverted light output under an applied electrical signal;

an electrical circuit in said sense signal generator, said electrical circuit being connected to an electrical sensing component at said catheter distal end and adapted to generate an electrical sense signal corresponding to a physiological condition to be sensed by said sensing component; and said electrical circuit being connected to provide said electrical sense signal to said optical modulator in order to modulate said diverted light output into a sensing optical signal;

said electrical circuit including means for converting said electrical sense signal from analog to digital form.

19. An opto-electric medical stimulation and sensing system having a photonic catheter containing one or more optical conductors for conducting light energy in two directions between electronics at a proximal end of said catheter and electrical stimulation and sensing components at a distal end of said catheter, comprising:

an optical sense signal generator located at said catheter distal end;

an optical unit in said sense signal generator adapted to receive a light input delivered from said catheter proximal end by one of said optical conductors and to transmit a first portion of said light input as a transmitted light output to an opto-electrical converter for conversion into electrical stimulation signals while diverting a second portion of said light input as a diverted light output;

an optical modulator in said sense signal generator positioned to receive said diverted light output and being adapted to modulate said diverted light output under an applied electrical signal;

an electrical circuit in said sense signal generator, said electrical circuit being connected to an electrical sensing component at said catheter distal end and adapted to generate an electrical sense signal corresponding to a physiological condition to be sensed by said sensing component; and said electrical circuit being connected to provide said electrical sense signal to said optical modulator in order to modulate said reflected light output into a sensing optical signal;

said optical unit being an optical homogenizer.

20. The opto-electric medical stimulation and sensing system as claimed in claim 19, wherein said optical unit is a prismatic optical homogenizer having a first end adapted to receive said light input and a second end having a partially reflective coating thereon for reflecting said second portion of said light input to said first end.

21. The opto-electric medical stimulation and sensing system as claimed in claim 20, wherein said partially reflective coating comprises a partially reflective material covering all of said second end.

22. The opto-electric medical stimulation and sensing system as claimed in claim 20, wherein said partially reflective coating comprises a fully reflective material covering a peripheral portion of said second end while leaving uncovered a central portion of said second end for transmitting said second portion of said light input.

23. The opto-electric medical stimulation and sensing system as claimed in claim 19, wherein said electrical circuit comprises means for conditioning a physiological sense signal generated via interaction of said sensing component with body tissue into said electrical sense signal.

24. The opto-electric medical stimulation and sensing system as claimed in claim 19, wherein said electrical circuit comprises means for obtaining electrical power from said transmitted light output.

25. An opto-electric medical stimulation and sensing system having a photonic catheter containing one or more optical conductors for conducting light energy in two directions between electronics at a proximal end of said catheter and electrical stimulation and sensing components at a distal end of said catheter, comprising:

an optical sense signal generator located at said catheter distal end;

an optical unit in said sense signal generator adapted to receive a light input delivered from said catheter proximal end by one of said optical conductors and to transmit a first portion of said light input as a transmitted light output to an onto-electrical converter for conversion into electrical stimulation signals while diverting a second portion of said light input as a diverted light output;

an optical modulator in said sense signal generator positioned to receive said diverted light output and being adapted to modulate said diverted light output under an applied electrical signal;

an electrical circuit in said sense signal generator, said electrical circuit being connected to an electrical sensing component at said catheter distal end and adapted to generate an electrical sense signal corresponding to a physiological condition to be sensed by said sensing component; and said electrical circuit being connected to provide said electrical sense signal to said optical modulator in order to modulate said reflected light output into a sensing optical signal;

said optical modulator being composed of a crystalline material having electrically controllable optical properties.

26. The opto-electric medical stimulation and sensing system as claimed in claim 25, wherein said crystalline material is selected from the group consisting of lithium niobate, indium phosphide and gallium arsenide.

27. An opto-electric medical stimulation and sensing system having a photonic catheter containing one or more optical conductors for conducting light energy in two directions between electronics at a proximal end of said catheter and electrical stimulation and sensing components at a distal end of said catheter, comprising:

an optical sense signal generator located at said catheter distal end;

an optical unit in said sense signal generator adapted to receive a light input delivered from said catheter proximal end by one of said optical conductors and to transmit a first portion of said light input as a transmitted light output to an opto-electrical converter for conversion into electrical stimulation signals while diverting a second portion of said light input as a diverted light output;

an optical modulator in said sense signal generator positioned to receive said diverted light output and being adapted to modulate said diverted light output under an applied electrical signal;

an electrical circuit in said sense signal generator, said electrical circuit being connected to an electrical sensing component at said catheter distal end and adapted to generate an electrical sense signal corresponding to a physiological condition to be sensed by said sensing component; and said electrical circuit being connected to provide said electrical sense signal to said optical modulator in order to modulate said reflected light output into a sensing optical signal;

said electrical circuit including means for converting said electrical sense signal from analog to digital form.

28. An optical device adapted to operate at the distal end of a photonic catheter having one or more optical conductors for conducting light energy in two directions between electronics at a proximal end of the photonic catheter and electrical components at the distal end of the photonic catheter, comprising:

an opto-electrical converter to convert received light into electrical signals;

an optical unit adapted to receive light delivered from the proximal end of the photonic catheter via an optical conductor;

said optical unit transmitting a first portion of the received light as transmitted light out to said opto-electrical converter while substantially simultaneously diverting a second portion of the received light;

an optical modulator positioned to receive the light diverted by said optical unit; and a sensor, operatively connected to said optical modulator, to generate a physiological sense signal corresponding to a sensed physiological condition;

said optical modulator modulating the diverted light based upon the physiological sense signal generated by said sensor;

said optical unit being an optical homogenizer.

29. The optical device as claimed in claim 28, wherein said optical unit is a prismatic optical homogenizer having a first end adapted to receive the light and a second end having a partially reflective coating thereon for reflecting a portion of the light to said first end.

30. The optical device as claimed in claim 29, wherein said partially reflective coating comprises a partially reflective material covering all of said second end.

31. The optical device as claimed in claim 29, wherein said partially reflective coating comprises a fully reflective material covering a peripheral portion of said second end while leaving uncovered a central portion of said second end for transmitting a portion of the light.

32. The optical device as claimed in claim 28, wherein said sensor comprises means for conditioning the generated physiological sense signal.

33. The optical device as claimed in claim 28, wherein said sensor is operatively connected to said opto-electrical converter to receive electrical power therefrom.

34. An optical device adapted to operate at the distal end of a photonic catheter having one or more optical conductors for conducting light energy in two directions between electronics at a proximal end of the photonic catheter and electrical components at the distal end of the photonic catheter, comprising:

an opto-electrical converter to convert received light into electrical signals;

an optical unit adapted to receive light delivered from the proximal end of the photonic catheter via an optical conductor;

said optical unit transmitting a first portion of the received light as transmitted light out to said opto-electrical converter while substantially simultaneously diverting a second portion of the received light;

an optical modulator positioned to receive the light diverted by said optical unit; and a sensor, operatively connected to said optical modulator, to generate a physiological sense signal corresponding to a sensed physiological condition;

said optical modulator modulating the diverted light based upon the physiological sense signal generated by said sensor;

said optical modulator being composed of a crystalline material having electrically controllable optical properties.

35. The optical device as claimed in claim 34, wherein said crystalline material is selected from the group consisting of lithium niobate, indium phosphide, and gallium arsenide.

36. An optical device adapted to operate at the distal end of a photonic catheter having one or more optical conductors for conducting light energy in two directions between electronics at a proximal end of the photonic catheter and electrical components at the distal end of the photonic catheter, comprising:

an opto-electrical converter to convert received light into electrical signals;

an optical unit adapted to receive light delivered from the proximal end of the photonic catheter via an optical conductor;

said optical unit transmitting a first portion of the received light as transmitted light out to said opto-electrical converter while substantially simultaneously diverting a second portion of the received light;

an optical modulator positioned to receive the light diverted by said optical unit; and a sensor, operatively connected to said optical modulator, to generate a physiological sense signal corresponding to a sensed physiological condition;

said optical modulator modulating the diverted light based upon the physiological sense signal generated by said sensor;

said sensor including means for converting the generated physiological sense signal into a digital signal.

* * * * *